(12) United States Patent
Allard et al.

(10) Patent No.: US 8,455,189 B2
(45) Date of Patent: Jun. 4, 2013

(54) USE OF HE4 FOR ASSESSMENT OF BREAST CANCERS

(76) Inventors: Jeffrey W. Allard, Malverne, PA (US); Thorsten Verch, Malverne, PA (US); Curtis Glover, Malverne, PA (US)

( * ) Notice: Subject to any disclaimer, the term of this patent is extended or adjusted under 35 U.S.C. 154(b) by 575 days.

(21) Appl. No.: 12/593,625

(22) PCT Filed: Mar. 31, 2008

(86) PCT No.: PCT/US2008/004176
§ 371 (c)(1),
(2), (4) Date: Aug. 23, 2010

(87) PCT Pub. No.: WO2008/121391
PCT Pub. Date: Oct. 9, 2008

(65) Prior Publication Data
US 2010/0311099 A1    Dec. 9, 2010

Related U.S. Application Data

(60) Provisional application No. 60/908,845, filed on Mar. 29, 2007.

(51) Int. Cl.
*G01N 31/00* (2006.01)
*G01N 33/00* (2006.01)

(52) U.S. Cl.
USPC ............................. 435/6.1; 435/69.1; 436/86

(58) Field of Classification Search
USPC ....................................... 435/69.1, 6; 436/86
See application file for complete search history.

(56) References Cited

FOREIGN PATENT DOCUMENTS

| WO | WO03004989 | 1/2003 |
|---|---|---|
| WO | WO2004063355 | 7/2004 |
| WO | WO2006135886 | 12/2006 |

OTHER PUBLICATIONS

Bouchard et al., Lancet Oncology, 7, 167-174, 2006.*
Galgano et al., "Comprehensive Analysis of HE4 Expression in Normal and Malignant Human Tissues", 19 Modern Pathology, 847-853 (2006).

* cited by examiner

*Primary Examiner* — Maryam Monshipouri
(74) *Attorney, Agent, or Firm* — Duane Morris LLP

(57) ABSTRACT

The disclosure relates to use of the HE4 marker to assess breast cancer in a patient. The disclosure also relates to using HE4 and other tumors markers for diagnosis, grading and staging of breast cancers. The disclosure also relates to determining prognosis and treatment effectiveness of a patient who has been diagnosed with breast cancer.

13 Claims, 2 Drawing Sheets

Figure 1:
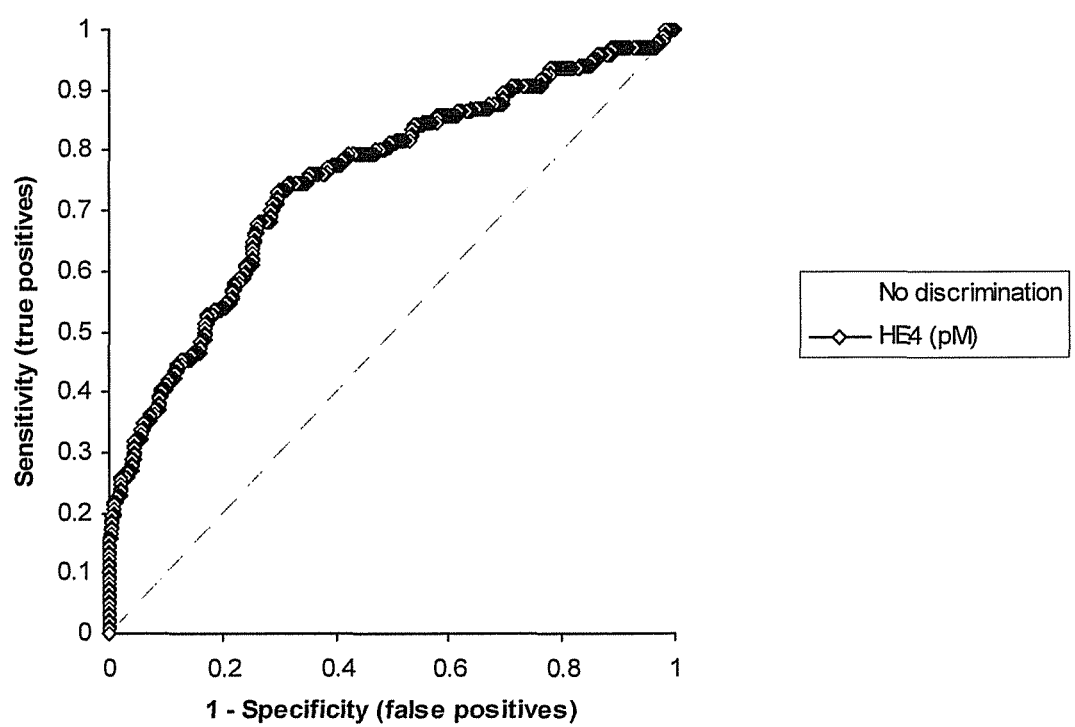

Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asn Cys Thr Gln Glu
        35                  40                  45

Cys Val Ser Asp Ser Glu Cys Ala Asp Asn Leu Lys Cys Cys Ser Ala
        50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
            85                  90                  95

Cys Gln Val Asp Ser Gln Cys Pro Gly Gln Met Lys Cys Cys Arg Asn
            100                 105                 110

Gly Cys Gly Lys Val Ser Cys Val Thr Pro Asn Phe
            115                 120

Figure 2

Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asn Cys Thr Gln Glu
        35                  40                  45

Cys Val Ser Asp Ser Glu Cys Ala Asp Asn Leu Lys Cys Cys Ser Ala
        50                  55                  60

Gly Cys Ala Thr Phe Cys Leu Leu Cys Pro Asn Asp Lys Glu Gly Ser
65                  70                  75                  80

Cys Pro Gln Val Asn Ile Asn Phe Pro Gln Leu Gly Leu Cys Arg Asp
            85                  90                  95

Gln Cys Gln Val Asp Thr Gln Cys Pro Gly Gln Met Lys Cys Cys Arg
            100                 105                 110

Asn Gly Cys Gly Lys Val Ser Cys Val Thr Pro Asn Phe
            115                 120                 125

Figure 3

USE OF HE4 FOR ASSESSMENT OF BREAST CANCERS

RELATED APPLICATIONS

This application is a 371 National Stage of International Application No. PCT/US2008/004176, filed Mar. 31, 2008, which claims the benefit of U.S. Provisional Application No. 60/908,845, filed Mar. 29, 2007. The aforementioned patent applications are expressly incorporated herein by reference in their entireties.

BACKGROUND OF THE DISCLOSURE

The disclosure relates generally to the field of diagnosis, grading, staging, and prognosis of cancer. More particularly, this disclosure relates to the field of breast cancers. This disclosure further relates to the field of diagnosis, grading, staging, and prognosis using protein expression.

Cancer includes a broad range of diseases, affecting approximately one in four individuals worldwide. The severity of the adverse impact of cancer is profound, influencing medical policy and procedure as well as society generally. Because a hallmark of many types of cancer is rapid and unregulated proliferation of malignant cells, an overarching problem in improving approaches to cancer is the need for early detection and diagnosis. Early detection is well regarded as the best means to reduce cancer mortality. In response, numerous attempts have been made to develop accurate and reliable criteria for diagnosing the presence of a malignant condition. In particular, investigations have been directed to the use of serologically defined antigenic markers known as tumor associated antigens, which are either uniquely expressed by cancer cells or are present at markedly higher levels in subjects having a malignant condition.

However, due to the high heterogeneity of tumor associated antigen expression, for example the extreme diversity of carcinoma antigens, there is a need for additional tumor markers that are useful in cancer diagnosis. Many monoclonal antibodies reactive with carcinoma associated antigens are known. Such monoclonal antibodies bind to a variety of different carcinoma-associated antigens including glycoproteins, glycolipids, and mucins. Many such monoclonal antibodies recognize tumor-associated antigens that exhibit restricted expression on some, but not other, tumors originating in a given cell lineage or tissue type.

There are relatively few examples of tumor associated antigens that appear to be useful for identifying a particular type of malignancy. Monoclonal antibody B72.3, for example, specifically binds to a high molecular mass (>106 Da) tumor-associated mucin antigen that is selectively expressed on a number of different carcinomas, including most if not all ovarian carcinomas and an overwhelming majority of non-small cell lung carcinomas, colon carcinomas and breast carcinomas. Nevertheless, detection of cell-associated tumor markers such as the mucin antigen recognized by B72.3 following surgical resection of a tumor may be of limited usefulness for diagnostic screening, in which early detection of a malignant condition prior to accumulation of substantial tumor mass is preferred.

An alternative to the diagnosis of a particular type of cancer by screening surgically resected specimens for tumor associated antigens, where invasive surgery is usually indicated only after detection of an accumulated tumor mass, would be to provide compositions and methods for detecting such antigens in samples obtained from subjects by non-invasive or minimally invasive procedures. In ovarian, endometrial, and other carcinomas, for example, there are currently a number of soluble tumor associated antigens that are detectable in samples of readily obtained biological fluids such as serum or mucosal secretions. One such marker is CA125, a carcinoma-associated antigen that is also shed into the bloodstream, where it is detectable in serum (e.g., Bast et al., 1983 N. Eng. J. Med. 309:883; Lloyd et al., 1997 Int. J. Canc. 71:842). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN) and placental alkaline phosphatase (PLAP), in an effort to provide diagnostic and/or prognostic profiles of ovarian, endometrial, and other carcinomas (e.g., Sarandakou et al., 1997 Acta Oncol. 36:755; Sarandakou et al., 1998 Eur. J. Gynaecol. Oncol. 19:73; Meier et al., 1997 Anticanc. Res. 17(4B):2945; Kudoh et al., 1999 Gynecol. Obstet. Invest. 47:52; Ind et al., 1997 Br. J. Obstet. Gynaecol. 104:1024; Bell et al. 1998 Br. J. Obstet. Gynaecol. 105:1136; Cioffi et al., 1997 Tumori 83:594; Meier et al. 1997 Anticanc. Res. 17(4B):2949; Meier et al., 1997 Anticanc. Res. 17(4B):3019).

Elevated levels of serum CA125 alone or in combination with other known indicators, however, do not provide a definitive diagnosis of malignancy, or of a particular malignancy such as breast carcinoma. For example, elevated CA125, CEA and SCC in vaginal fluid and serum correlate most strongly with inflammation in benign gynecological diseases, relative to cervical cancer and genital tract cancers (e.g., Moore et al., 1998 Infect. Dis. Obstet. Gynecol. 6:182; Sarandakou et al., 1997 Acta Oncol. 36:755). Elevated serum CA125 can also accompany neuroblastoma, and elevated CEA and SCC levels can accompany colorectal cancer. Another marker, the differentiation antigen mesothelin, is expressed on the surfaces of normal mesothelial cells and also on certain cancer cells, including epithelial ovarian tumors and mesotheliomas. Compositions and methods pertaining to mesothelin (Chang et al., 1992 Canc. Res. 52:181; Chang et al., 1992 Int. J. Canc. 50:373; Chang et al., 1992 Int. J. Canc. 51:548; Chang et al., 1996 Proc. Nat. Acad. Sci. USA 93:136; Chowdhury et al., 1998 Proc. Nat. Acad. Sci. USA 95:669; Yamaguchi et al., 1994 J. Biol. Chem. 269:805; Kojima et al., 1995 J. Biol. Chem. 270:21984) and structurally related mesothelin related antigen (MRA; see, e.g., Scholler et al., 1999 Proc. Nat. Acad. Sci. USA 96:11531) are known in the art, including uses in cancer detection and therapies as described in WO 00/50900 and in U.S. application Ser. No. 09/513,597. There is a compelling need for additional markers useful in multiple marker diagnostic screening.

SUMMARY OF THE DISCLOSURE

The subject matter of this disclosure includes a method of assessing whether a patient is afflicted with a breast cancer. The method includes assessing expression of HE4 in a sample (e.g., a solid tissue sample, a body fluid sample, or a sample of a fluid that has been contacted with a relevant portion of the patient's body) obtained from the patient. Elevated expression of HE4 is an indication that the patient is afflicted with a breast cancer. If desired, the level of HE4 expression can be compared with a reference value, such as a reference value that corresponds to HE4 expression in patients who are not afflicted with a breast cancer. Alternatively, expression of HE4 in the sample can be compared with expression of HE4 in an earlier sample obtained at an earlier time from the patient. One or more additional markers corresponding to occurrence of a breast cancer can also be assessed.

The disclosure also relates to a method of assessing the response of a patient afflicted with a breast cancer to a treatment. The method includes assessing expression of HE4 in samples obtained from the patient at different times during treatment. Decreased expression of HE4 at the later time (or a decrease in expression over time) indicates that the patient is responding to the treatment.

The disclosure further relates to a method of assessing recurrence in a patient who has been treated for a breast cancer. The method includes assessing expression of HE4, alone or in combination with one or more second markers, in samples obtained from the patient following treatment. Elevated expression of HE4 indicates that the breast cancer is recurring in the patient, and elevated expression of the second marker is a further indication that the breast cancer is recurring in the patient. Expression of HE4 can, for example, be assessed multiple times following the treatment. Increasing expression of HE4 over time indicates that the breast cancer is recurring in the patient.

In another embodiment, the disclosure relates to a method of assessing the likelihood that a patient will develop a breast cancer. The method includes assessing expression of HE4, alone or in combination with one or more second markers, in a sample obtained from the patient. Elevated expression of HE4 is correlated with increased likelihood that the patient will develop a breast cancer, and elevated expression of the second marker is a further indication that the patient will develop a breast cancer.

In yet another embodiment, the disclosure pertains to a method of staging and/or grading a tumor in a patient afflicted with a breast cancer. The method includes assessing expression of HE4, alone or in combination with one or more second markers, in a sample obtained from the patient. Increased expression of HE4 (and the second markers, if assessed) correlates with and indicates a more advanced stage of the cancer and/or a higher grade of the of the cancer.

Still another aspect of the subject matter disclosed herein pertains to a method for assessing the need of a patient diagnosed with a breast cancer for a therapeutic intervention (e.g., chemotherapy). The method includes assessing expression of HE4, alone or in combination with one or more second markers, in a sample obtained from the patient. Elevated expression of HE4 (and the second markers, if assessed) indicates need of the patient for the therapeutic intervention.

BRIEF SUMMARY OF THE SEVERAL FIGURES

FIG. 1 is a summary of area under curve (AUC) analysis of ROC (Receiver Operating Characteristic) curve data obtained in the experiments described herein in Example 1.

FIG. 2 is the amino acid sequence (SEQ ID NO: 1) of HE4a protein, as disclosed (as each of SEQ ID NOs: 11 and 13) in U.S. Pat. No. 7,270,960, which also discloses two naturally-occurring cDNA sequences corresponding to this protein FIG. 3 is the amino acid sequence (SEQ ID NO: 2) of HE4 protein, as deduced by Kirchhoff et al., 1991, Biol. Reprod. 45:350-357.

DETAILED DESCRIPTION

The disclosure relates to the discovery that the HE4 antigen is an indicator of the existence, grade, and stage of breast cancers.

The subject matter of this disclosure relates generally to assessment of breast cancer in women using the HE4 marker or a combination of HE4 and other biological markers. Assessing HE4 with one or more additional makers of breast cancers can be used to diagnose occurrence of such cancers in a human patient, and to assess the response of such cancers to treatments of various types. Furthermore, assessment of these markers can be used to monitor recurrence of such cancers in a patient or to assess the likelihood that a patient will develop such cancers. Any known breast cancer marker can be used as a secondary marker.

Definitions

As used herein by the term a "sample" is meant material which can be specifically related to a patient and from which specific information about the patient can be determined, calculated or inferred. A sample can be composed in whole or in part of biological material from the patient (e.g., a solid tissue sample obtained from a breast biopsy of a woman). A sample can also be material that has contacted the patient in a way that allows tests to be conducted on the sample which provides information about the patient (e.g., a ductal lavage fluid). A sample can also be a first material that has contacted a second material that is not of the patient but allows the first material to then be tested to determine information about the patient (e.g., the first sample can be a wash of a probe, scalpel, or biopsy needle that has contacted a tissue of a woman). A sample can contact sources of biologic material other than the patient provided that one skilled in the art can nevertheless determine information about the patient from the sample. It is also understood that extraneous material or information that is not the sample can be utilized to conclusively link the patient to the sample. For a non-limiting example, a double blind test requires a chart or database to match a sample with a patient.

As used herein by the term "patient" it is meant an organism that is the subject of an assay to determine information about the organism. While, in most embodiments of the methods disclosed herein the patient is a human and a woman, the methods are not limited for use with an individual human, male or female. The sample used herein can be obtained from a group of humans (i.e., without identifying an individual human). The sample can also correspond to a part of a human, such as a breast tissue. For non-limiting examples of this embodiment, the sample can be a tissue sample not linked to a human body, or a transformed cell line.

As used herein the term "reference value" means a value that statistically correlates to a particular outcome when compared to an assay result. In some embodiments, the reference value is determined from statistical review of studies that compare HE4a expression with known clinical outcomes. Some such studies are presented in the Examples section herein. However, studies from the literature and the experience of users of the methods disclosed herein can also be used to produce or adjust a reference value. Reference values can also be determined from consideration of cases and results that are particularly relevant to the patient's medical history, genetics, age and other factors.

As used herein the term "body fluid" it is meant a material obtained from a human that is substantially fluid in consistency, but can have solid or particulate matter associated with it. A body fluid can also contain material and portions that are not from the patient. For instance a body fluid can be diluted with water, or can contain a preservative, such as EDTA. Non-limiting examples of body fluids include blood and serum. Likewise, breast secretions, breast milk, ductal lavage fluid, and nipple aspirate fluid can be used as the sample the methods disclosed herein. In view of the fact that breast cancers can metastasize or otherwise spread to other regions of the body, additional body fluids such as urine, cerebrospinal fluid, saliva, serosal fluids, plasma, lymph, mucosal secretions of the secretory tissues and organs, vaginal secretions, tears, and ascites fluids such as those associated with non-solid tumors can be used as samples. Additional examples include fluids of the pleural, pericardial, peritoneal, abdominal and other body cavities, and the like. Biological fluids can further include liquid solutions contacted with a subject or biological source, for example, cell and organ culture medium including cell or organ conditioned medium, lavage fluids and the like.

A sample is obtained from a patient "during treatment" if the sample is obtained as a prelude to administration, at the time of administration, or following administration of a therapeutic composition or method or during the period of follow-up that occurs thereafter. Use of this term explicitly encompasses situations in which samples are obtained prior to and after administration of the treatment (i.e., to assess effectiveness of the treatment or recurrence), as well as situations in which multiple samples are taken intermittently during an extended course of treatment.

DETAILED DESCRIPTION

The methods disclosed herein pertain to HE4, a member of the "four-disulfide core" family of proteins as described herein. The "four-disulfide core" family of proteins comprises a heterogeneous group of small acid- and heat-stable molecules of divergent function and which includes human epididymal four-disulfide core protein, or "HE4" (Kirchhoff et al., 1991 Biol. Reprod. 45:350-357; Wang et al., 1999 Gene 229:101; Schummer et al., 1999 Gene 238:375).

HE4 cDNA was first isolated from human epididymis (Kirchhoff et al., 1991 Biol. Reprod. 45:350-357), and HE4 cDNA was later detected with high frequency in cDNA libraries constructed from ovarian carcinomas (Wang et al., 1999 Gene 229:101; Schummer et al., 1999 Gene 238:375). The corrected sequence of HE4a was disclosed in Hellstrom et al., 2003, Canc. Res. 63:3695-3700 and in U.S. Pat. No. 7,270,960, which are incorporated herein by reference. HE4a exhibits an amino acid sequence that is highly similar to, but distinct from, the deduced sequence of the molecule that was referred to as HE4 in earlier publications.

For the purposes of this disclosure, detection of either HE4 or HE4a are considered synonymous, and are referred to synonymously herein as "HE4". The amino acid sequences of HE4 (SEQ ID NO: 2; as deduced by Kirchhoff et al., 1991, Biol. Reprod. 45:350-357) and the corrected sequence HE4a (SEQ ID NO: 1; as disclosed in U.S. Pat. No. 7,270,960) are shown in FIGS. 3 and 2, respectively.

The methods disclosed herein also pertain to compositions and methods for detection of cell surface and/or soluble forms of HE4 that occur naturally in subjects, including elevated levels of such polypeptides in subjects having certain cancers, such as breast cancers. This disclosure therefore provides useful compositions and methods for the detection and diagnosis of a malignant condition in a subject by specific detection of such cell surface and/or soluble HE4 polypeptides.

According to the methods disclosed herein, a soluble human HE4 antigen polypeptide (or HE4 polypeptide) can be detected in a biological sample from a subject or biological source. Biological samples can be provided by obtaining a blood sample, biopsy specimen, tissue explant, organ culture, biological fluid or any other tissue or cell preparation from a subject or a biological source. The subject or biological source can be a human or non-human animal, a primary cell culture or culture adapted cell line including but not limited to genetically engineered cell lines that can contain chromosomally integrated or episomal recombinant nucleic acid sequences, immortalized or immortalizable cell lines, somatic cell hybrid cell lines, differentiated or differentiable cell lines, transformed cell lines and the like. In certain embodiments of the methods disclosed herein, the subject or biological source can be suspected of having or being at risk for having a malignant condition, which can be a breast cancer such as a breast carcinoma, or the subject or biological source can be known to be free of a risk or presence of such diseases.

In some embodiments, the biological sample includes at least one cell from a subject or biological source, and in other embodiments the biological sample is a biological fluid containing another tumor marker, such as CA-125. Biological fluids are typically liquids at physiological temperatures and can include naturally occurring fluids present in, withdrawn from, expressed or otherwise extracted from a subject or biological source. Certain biological fluids derive from particular tissues, organs or localized regions and certain other biological fluids can be more globally or systemically situated in a subject or biological source. Examples of body fluids include blood and serum. Likewise, breast secretions, breast milk, ductal lavage fluid, and nipple aspirate fluid are particularly well suited to the methods disclosed herein. In certain circumstances, body fluids such as urine, cerebrospinal fluid, saliva, serosal fluids, plasma, lymph, mucosal secretions of the secretory tissues and organs, vaginal secretions, tears, and ascites fluids such as those associated with non-solid tumors are also suitable. Additional examples include fluids of the pleural, pericardial, peritoneal, abdominal and other body cavities, and the like. Biological fluids can further include liquid solutions contacted with a subject or biological source, for example, cell and organ culture medium including cell or organ conditioned medium, lavage fluids and the like. In other embodiments the biological sample is a cell-free liquid solution, such as blood serum, plasma, or the supernatant of centrifuged urine.

In other embodiments the biological sample comprises an intact cell, and in other embodiments the biological sample includes a cell extract containing a nucleic acid sequence encoding a HE4 antigen polypeptide having the amino acid sequence set forth in SEQ ID NOs: 1 or 2 (U.S. Pat. No. 7,270,960 discloses the cDNA sequences corresponding to these polypeptide sequences) or a fragment thereof. In still other embodiments of the methods disclosed herein, it is desired that cells are physically or chemically ruptured or lysed before assaying to provide cell contents for analysis.

A "molecule naturally occurring in soluble form" in a sample can be a soluble protein, polypeptide, peptide, amino acid, or derivative thereof; a lipid, fatty acid or the like, or derivative thereof; a carbohydrate, saccharide or the like or derivative thereof, a nucleic acid, nucleotide, nucleoside, purine, pyrimidine or related molecule, or derivative thereof, or the like; or any combination thereof such as, for example, a glycoprotein, a glycolipid, a lipoprotein, a proteolipid, or any other biological molecule that is a soluble or cell-free constituent of a biological sample as provided herein. A "molecule naturally occurring in soluble form" further refers to a molecule that is in solution or present in a biological sample, including a biological fluid as provided herein, and that is not bound to the surface of an intact cell. For example, a molecule naturally occurring in soluble form can include but need not be limited to a solute; a component of a macromolecular complex; a material that is shed, secreted or exported from a cell; a colloid; a microparticle or nanoparticle or other fine suspension particle; or the like.

The presence of a malignant condition in a subject refers to the presence of dysplastic, cancerous and/or transformed cells in the subject, including, for example neoplastic, tumor, non-contact inhibited or oncogenically transformed cells, or the like. By way of illustration and not limitation, in the context of the methods disclosed herein a malignant condition can refer further to the presence in a subject of cancer cells that are capable of secreting, shedding, exporting or releasing a HE4 antigen polypeptide (or a HE4 polypeptide) in such a manner that elevated levels of such a polypeptide are detectable in a biological sample from the subject. In some embodiments, such cancer cells are malignant epithelial cells such as carcinoma cells, and in some embodiments such cancer cells are malignant mesothelioma cells, which are transformed variants of squamous cell epithelial or mesothelial cells that are found, for example, lining pleural, pericardial, peritoneal, abdominal and other body cavities.

The tumor cells, the presence of which signifies the presence of a malignant condition, can be breast cancer cells, including primary and metastatic breast cancer cells. Criteria for classifying a malignancy as a breast cancer are well known in the art as are the establishment and characterization of human breast cancer cell lines from primary and metastatic tumors.

Reference values are provided in the examples contained herein. Such values are suitable for practice of the methods disclosed herein. However it should be noted that the use of the methods disclosed herein is not limited to those reference values or that data. Those skilled in the art can obtain a reference value for their particular needs. Such a reference value can be obtained by analyzing HE4 expression in patients as they undergo biopsy procedures for breast tissue samples (e.g., "lumps" or radiologically unusual masses) suspected of being malignant. Methods of obtaining such reference values are contained herein and provided in the examples. Users of the methods disclosed herein may wish to obtain different reference value than provided herein to focus on specific categories of patients. In is foreseen that such categories could include age, genetic background, risk of cancer, medical history, blood type, physical characteristics such as body mass, and other categories.

As provided herein, the method of screening for the presence of a malignant condition in a subject can employ an antibody specific for a HE4 antigen polypeptide or an antibody specific for a HE4 polypeptide.

Antibodies that are specific for a HE4 antigen polypeptide (or a HE4 polypeptide) are readily generated as monoclonal antibodies or as polyclonal antisera, or can be produced as genetically engineered immunoglobulins (Ig) that are designed to have desirable properties using methods well known in the art. For example, by way of illustration and not limitation, antibodies can include recombinant IgGs, chimeric fusion proteins having immunoglobulin derived sequences or "humanized" antibodies (see, e.g., U.S. Pat. Nos. 5,693,762; 5,585,089; 4,816,567; 5,225,539; 5,530,101; and references cited therein) that can all be used for detection of a human HE4 polypeptide according to the methods disclosed herein. Such antibodies can be prepared as provided herein, including by immunization with HE4 polypeptides as described below. For example, as provided herein, nucleic acid sequences encoding HE4 polypeptides are disclosed, such that those skilled in the art can routinely prepare these polypeptides for use as immunogens. For instance, monoclonal antibodies such as 2H5, 3D8 and 4H4, which are described in greater detail below, can be used to practice certain methods according to the methods disclosed herein.

The term "antibodies" includes polyclonal antibodies, monoclonal antibodies, fragments thereof such as F(ab')$_2$ and Fab fragments, as well as any naturally occurring or recombinantly produced binding partners, which are molecules that specifically bind a HE4 polypeptide. Antibodies are defined to be "immunospecific" or specifically binding if they bind HE4 polypeptide with a $K_a$ of greater than or equal to about $10^4$ M$^{-1}$, preferably of greater than or equal to about $10^5$ M$^{-1}$, more preferably of greater than or equal to about $10^6$ M$^{-1}$ and still more preferably of greater than or equal to about $10^7$ M$^{-1}$. Affinities of binding partners or antibodies can be readily determined using conventional techniques, for example those described by Scatchard et al., Ann. N.Y. Acad. Sci. 51:660 (1949). Determination of other proteins as binding partners of a HE4 polypeptide can be performed using any of a number of known methods for identifying and obtaining proteins that specifically interact with other proteins or polypeptides, for example, a yeast two-hybrid screening system such as that described in U.S. Pat. Nos. 5,283,173 and 5,468,614, or the equivalent. The methods disclosed herein also includes the use of a HE4 polypeptide, and peptides based on the amino acid sequence of a HE4 polypeptide, to prepare binding partners and antibodies that specifically bind to a HE4 polypeptide.

Antibodies can generally be prepared by any of a variety of techniques known to those of ordinary skill in the art (see, e.g., Harlow and Lane, Antibodies: A Laboratory Manual, Cold Spring Harbor Laboratory, 1988). In one such technique, an immunogen comprising a HE4 polypeptide, for example a cell having a HE4 polypeptide on its surface or an isolated HE4 polypeptide is initially injected into a suitable animal (e.g., mice, rats, rabbits, sheep and goats), preferably according to a predetermined schedule incorporating one or more booster immunizations, and the animals are bled periodically. Polyclonal antibodies specific for the HE4 polypeptide can then be purified from such antisera by, for example, affinity chromatography using the polypeptide coupled to a suitable solid support.

Monoclonal antibodies specific for HE4 polypeptides or variants thereof can be prepared, for example, using the technique of Kohler and Milstein (1976 Eur. J. Immunol. 6:511-519), and improvements thereto. Briefly, these methods involve the preparation of immortal cell lines capable of producing antibodies having the desired specificity (i.e., reactivity with the mesothelin polypeptide of interest). Such cell lines can be produced, for example, from spleen cells obtained from an animal immunized as described above. The spleen cells are then immortalized by, for example, fusion with a myeloma cell fusion partner, such as one that is syngeneic with the immunized animal. For example, the spleen cells and myeloma cells can be combined with a membrane fusion promoting agent such as polyethylene glycol or a nonionic detergent for a few minutes, and then plated at low density on a selective medium that supports the growth of hybrid cells, but not myeloma cells. An example of a selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferable. Hybridomas that generate monoclonal antibodies that specifically bind to HE4 polypeptides are contemplated by the methods disclosed herein.

Monoclonal antibodies can be isolated from the supernatants of growing hybridoma colonies. In addition, various techniques can be employed to enhance the yield, such as injection of the hybridoma cell line into the peritoneal cavity of a suitable vertebrate host, such as a mouse or other suitable host. Monoclonal antibodies can then be harvested from the ascites fluid or the blood. Contaminants can be removed from the antibodies by conventional techniques, such as chromatography, gel filtration, precipitation, and extraction. For example, antibodies can be purified by chromatography on immobilized Protein G or Protein A using standard techniques.

Within certain embodiments, antigen-binding fragments of antibodies can be used. Such fragments include Fab fragments, which can be prepared using standard techniques (e.g., by digestion with papain to yield Fab and Fc fragments). The Fab and Fc fragments can be separated by affinity chromatography (e.g., on immobilized protein A columns), using standard techniques. Such techniques are well known in the art, see, e.g., Weir, D. M., Handbook of Experimental Immunology, 1986, Blackwell Scientific, Boston.

Multifunctional fusion proteins having specific binding affinities for pre-selected antigens by virtue of immunoglobulin V-region domains encoded by DNA sequences linked in-frame to sequences encoding various effector proteins are known in the art, for example, as disclosed in EP-B1-0318554, U.S. Pat. Nos. 5,132,405, 5,091,513 and 5,476,786. Such effector proteins include polypeptide domains that can be used to detect binding of the fusion protein by any of a variety of techniques with which those skilled in the art will be familiar, including but not limited to a biotin mimetic sequence (see, e.g., Luo et al., 1998 J. Biotechnol. 65:225 and references cited therein), direct covalent modification with a detectable labeling moiety, non-covalent binding to a specific labeled reporter molecule, enzymatic modification of a detectable substrate or immobilization (covalent or non-covalent) on a solid-phase support.

Single chain antibodies for use in the methods disclosed herein can also be generated and selected by a method such as phage display (see, e.g., U.S. Pat. No. 5,223,409; Schlebusch et al., 1997 Hybridoma 16:47; and references cited therein). Briefly, in this method, DNA sequences are inserted into the gene III or gene VIII gene of a filamentous phage, such as M13. Several vectors with multicloning sites have been developed for insertion (McLafferty et al., Gene 128:29-36, 1993; Scott and Smith, Science 249:386-390, 1990; Smith and Scott, Methods Enzymol. 217:228-257, 1993). The inserted DNA sequences can be randomly generated or can be variants of a known binding domain for binding to a HE4 polypeptide. Single chain antibodies can readily be generated using this method. Generally, the inserts encode from 6 to 20 amino acids. The peptide encoded by the inserted sequence is displayed on the surface of the bacteriophage. Bacteriophage expressing a binding domain for a HE4 polypeptide are selected by binding to an immobilized HE4 polypeptide, for example a recombinant polypeptide, prepared using methods well known in the art and nucleic acid coding sequences as disclosed herein. Unbound phage are removed by a wash, typically containing 10 mM Tris, 1 mM EDTA, and without salt (e.g., NaCl) or with a low salt concentration. Bound phage are eluted with a salt containing buffer, for example. The NaCl concentration is increased in a step-wise fashion until all the phage are eluted. Typically, phage binding with higher affinity will be released by higher salt concentrations. Eluted phage are propagated in the bacteria host. Further rounds of selection can be performed to select for a few phage binding with high affinity. The DNA sequence of the insert in the binding phage is then determined. Once the predicted amino acid sequence of the binding peptide is known, sufficient peptide for use herein as an antibody specific for a HE4 polypeptide can be made either by recombinant means or synthetically. Recombinant means are used when the antibody is produced as a fusion protein. The peptide can also be generated as a tandem array of two or more similar or dissimilar peptides, in order to maximize affinity or binding.

To detect an antigenic determinant reactive with an antibody specific for a HE4 polypeptide, the detection reagent is typically an antibody, which can be prepared as described herein or by any of a variety of methods known in the art. There are a variety of assay formats known to those of ordinary skill in the art for using an antibody to detect a polypeptide in a sample, including but not limited to enzyme linked immunosorbent assay (ELISA), radioimmunoassay (RIA), immunofluorimetry, immunoprecipitation, equilibrium dialysis, immunodiffusion and other techniques. See, e.g., Harlow and Lane, Antibodies: A Laboratory Manual, Cold Spring Harbor Laboratory, 1988; Weir, D. M., Handbook of Experimental Immunology, 1986, Blackwell Scientific, Boston. For example, the assay can be performed in a Western blot format, wherein a protein preparation from the biological sample is submitted to gel electrophoresis, transferred to a suitable membrane and allowed to react with the antibody. The presence of the antibody on the membrane can then be detected using a suitable detection reagent, as is well known in the art and described below.

In another embodiment, the assay involves the use of an antibody immobilized on a solid support to bind to the target HE4 polypeptide and remove it from the remainder of the sample. The bound HE4 polypeptide can then be detected using a second antibody reactive with a distinct HE4 polypeptide antigenic determinant, for example, a reagent that contains a detectable reporter moiety. As a non-limiting example, according to this embodiment the immobilized antibody and the second antibody which recognize distinct antigenic determinants can be any two of the monoclonal antibodies designated 2H5, 3D8 and 4H4 (Fujirebio Diagnostics, Inc.). Alternatively, a competitive assay can be utilized, in which a HE4 polypeptide is labeled with a detectable reporter moiety and allowed to bind to the immobilized HE4 polypeptide specific antibody after incubation of the immobilized antibody with the sample. The extent to which components of the sample inhibit the binding of the labeled polypeptide to the antibody is indicative of the reactivity of the sample with the immobilized antibody, and as a result, indicative of the level of HE4 in the sample.

The solid support can be any material known to those of ordinary skill in the art to which the antibody can be attached, such as a test well in a microtiter plate, a nitrocellulose filter or another suitable membrane. Alternatively, the support can be a bead or disc, such as glass, fiberglass, latex or a plastic such as polystyrene or polyvinylchloride. The antibody can be immobilized on the solid support using a variety of techniques known to those in the art, which are amply described in the patent and scientific literature.

In certain embodiments, the assay for detection of HE4 antigen polypeptide in a sample is a two-antibody sandwich assay. This assay can be performed by first contacting a HE4 polypeptide-specific antibody (e.g., a monoclonal antibody such as 2H5, 3D8 or 4H4) that has been immobilized on a solid support, commonly the well of a microtiter plate, with the biological sample, such that a soluble molecule naturally occurring in the sample and having an antigenic determinant that is reactive with the antibody is allowed to bind to the immobilized antibody (e.g., a 30 minute incubation time at room temperature is generally sufficient) to form an antigen-antibody complex or an immune complex. Unbound constituents of the sample are then removed from the immobilized immune complexes. Next, a second antibody specific for a HE4 antigen polypeptide is added, wherein the antigen combining site of the second antibody does not competitively inhibit binding of the antigen combining site of the immobilized first antibody to a HE4 polypeptide (e.g., a monoclonal antibody such as 2H5, 3D8 or 4H4 that is not the same as the monoclonal antibody immobilized on the solid support). The second antibody can be detectably labeled as provided herein, such that it can be directly detected. Alternatively, the second antibody can be indirectly detected through the use of a detectably labeled secondary (or "second stage") anti-antibody, or by using a specific detection reagent as provided herein. The methods disclosed herein are not limited to any particular detection procedure, as those having familiarity with immunoassays will appreciate that there are numerous reagents and configurations for immunologically detecting a particular antigen (e.g., a mesothelin polypeptide) in a two-antibody sandwich immunoassay.

In certain embodiments of the methods disclosed herein using the two-antibody sandwich assay described above, the first, immobilized antibody specific for a HE4 antigen polypeptide is a polyclonal antibody and the second antibody specific for a HE4 antigen polypeptide is a polyclonal antibody. Any combination of non-competitive HE4 antibodies could be used with the methods disclosed herein. Including monoclonal antibodies, polyclonal antibodies and combinations thereof. In certain other embodiments of the methods disclosed herein the first, immobilized antibody specific for a HE4 antigen polypeptide is a monoclonal antibody and the second antibody specific for a HE4 antigen polypeptide is a polyclonal antibody. In certain other embodiments of the methods disclosed herein the first, immobilized antibody specific for a HE4 antigen polypeptide is a polyclonal antibody and the second antibody specific for a HE4 antigen polypeptide is a monoclonal antibody. In other embodiments of the methods disclosed herein the first, immobilized antibody specific for a HE4 antigen polypeptide is a monoclonal antibody and the second antibody specific for a HE4 antigen polypeptide is a monoclonal antibody. For example, in these embodiments it should be noted that monoclonal antibodies 2H5, 3D8 and 4H4 as provided herein recognize distinct and non-competitive antigenic determinants (e.g., epitopes) on HE4 polypeptides, such that any pairwise combination of these monoclonal antibodies can be employed. In other embodiments of the methods disclosed herein the first, immobilized antibody specific for a HE4 antigen polypeptide and/or the second antibody specific for a HE4 antigen polypeptide can be any of the kinds of antibodies known in the art and referred to herein, for example by way of illustration and not limitation, Fab fragments, F(ab')$_2$ fragments, immunoglobulin V-region fusion proteins or single chain antibodies. Those familiar with the art will appreciate that the methods disclosed herein encompass the use of other antibody forms, fragments, derivatives and the like in the methods disclosed and claimed herein.

In certain embodiments, the second antibody can contain a detectable reporter moiety or label such as an enzyme, dye, radionuclide, luminescent group, fluorescent group or biotin, or the like. Any reporter moiety or label could be used with the methods disclosed herein so long as the signal of such is directly related or proportional to the quantity of antibody remaining on the support after wash. The amount of the second antibody that remains bound to the solid support is then determined using a method appropriate for the specific detectable reporter moiety or label. For radioactive groups, scintillation counting or autoradiographic methods are generally appropriate. Antibody-enzyme conjugates can be prepared using a variety of coupling techniques (for review see, e.g., Scouten, W. H., Methods in Enzymology 135:30-65, 1987). Spectroscopic methods can be used to detect dyes (including, for example, colorimetric products of enzyme reactions), luminescent groups and fluorescent groups. Biotin can be detected using avidin or streptavidin, coupled to a different reporter group (commonly a radioactive or fluorescent group or an enzyme). Enzyme reporter groups can generally be detected by the addition of substrate (generally for a specific period of time), followed by spectroscopic, spectrophotometric or other analysis of the reaction products. Standards and standard additions can be used to determine the level of antigen in a sample, using well known techniques.

In another embodiment, the methods disclosed herein contemplate the use of a HE4 antigen polypeptide as provided herein to screen for the presence of a malignant condition by detection of immunospecifically reactive antibodies in a biological sample from a biological source or subject. According to this embodiment, a HE4 antigen polypeptide (or a fragment or variant thereof including a truncated HE4 antigen polypeptide as provided herein) is detectably labeled and contacted with a biological sample to detect binding to the HE4 antigen polypeptide of an antibody naturally occurring in soluble form in the sample. For example, the HE4 antigen polypeptide can be labeled biosynthetically by using the sequences disclosed herein in concert with well known methods such as incorporation during in vitro translation of a readily detectable (e.g. radioactively labeled) amino acid, or by using other detectable reporter moieties such as those described above. Without wishing to be bound by theory, this embodiment of the methods disclosed herein contemplate that certain HE4 polypeptides such as the HE4 fusion polypeptides disclosed herein, can provide peptides that are particularly immunogenic and so give rise to specific and detectable antibodies. For example, according to this theory certain HE4 fusion polypeptides can represent "non-self" antigens that provoke an avid immune response, while HE4 polypeptides that lack fusion domains can be viewed by the immune system as more resembling "self" antigens that do not readily elicit humoral or cell-mediated immunity.

As noted above, the methods disclosed herein pertain in part to the surprising finding that soluble forms of HE4 antigen polypeptides occur naturally in subjects, including elevated levels of such soluble HE4 polypeptides in subjects afflicted with breast cancer.

A method of screening for the presence of a breast cancer according to the methods disclosed herein can be further enhanced by the detection of more than one tumor associated marker in a biological sample from a subject. Accordingly, certain embodiments the methods disclosed herein provide a method of screening that, in addition to detecting reactivity of a naturally occurring soluble sample component with an antibody specific for a HE4 antigen polypeptide, also includes detection of at least one additional soluble marker of a malignant condition using established methods as known in the art and provided herein. These additional soluble tumor associated antigens can include, but need not be limited to, mesothelin and mesothelin related antigen, CEA, CA125, sialyl TN, SCC, TPS and PLAP, (see e.g., Bast et al., 1983 N. Eng. J. Med. 309:883; Lloyd et al., 1997 Int. J. Canc. 71:842; Sarandakou et al., 1997 Acta Oncol. 36:755; Sarandakou et al., 1998 Eur. J. Gynaecol. Oncol. 19:73; Meier et al., 1997 Anticanc. Res. 17(4B):2945; Kudoh et al., 1999 Gynecol. Obstet. Invest. 47:52; Ind et al., 1997 Br. J. Obstet. Gynaecol. 104: 1024; Bell et al. 1998 Br. J. Obstet. Gynaecol. 105:1136; Cioffi et al., 1997 Tumori 83:594; Meier et al. 1997 Anticanc. Res. 17(4B):2949; Meier et al., 1997 Anticanc. Res. 17(4B): 3019) and can further include any known marker the presence of which in a biological sample can be correlated with the presence of a breast tumor, as provided herein.

Alternatively, nucleic acid sequences encoding HE4 polypeptides can be detected, using standard hybridization and/or polymerase chain reaction (PCR) techniques. Suitable probes and primers can be designed by those of ordinary skill in the art based on the HE4 cDNA sequences provided herein. Assays can generally be performed using any of a variety of samples obtained from a biological source, such as eukaryotic cells, bacteria, viruses, extracts prepared from such organisms and fluids found within living organisms.

EXAMPLES

General Methods

Standard recombinant DNA and molecular cloning techniques used in the Examples are well known in the art and are described by Sambrook, J., Fritsch, E. F. and Maniatis, T. Molecular Cloning: A Laboratory Manual; Cold Spring Harbor Laboratory Press: Cold Spring Harbor, (1989) (Maniatis) and by T. J. Silhavy, M. L. Berman, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

The meaning of abbreviations is as follows: "h" means hour(s), "min" means minute(s), "sec" means second(s), "d" means day(s), "mL" means milliliters, "L" means liters, "U" means units, "pM" means picomolar, "ROC" means receiver operating characteristic, "AUC" means area under curve, "StDev" means standard deviation, "Min" means minimum "Max" means maximum and "p" means p-value.

The subject matter of this disclosure is now described with reference to the following Examples. These Examples are provided for the purpose of illustration only, and the subject matter is not limited to these Examples, but rather encompasses all variations which are evident as a result of the teaching provided herein.

Example 1

Utility of serum tumor marker HE4 in patients with breast cancer.

HE4 concentrations in serum of breast cancer patients were compared with that of healthy control patients. The results are shown in FIG. 1. The following table represents an ROC curve analysis of the HE4 data shown in FIG. 1, comparing healthy patients with breast cancer patients.

| Curve | Area | SE | p | 95% CI of Area | Condition = Breast Cancer |
|---|---|---|---|---|---|
| HE4 (pM) | 0.750 | 0.0251 | <0.0001 | 0.701 to 0.800 | have higher values |

The data analysis demonstrates that expression of HE4 in serum is elevated in approximately 32% of breast cancers (95% specificity). An ROC curve analysis resulted in an area under the curve AUC=0.75, which demonstrates that measurement of HE4 concentrations in serum and other fluids can be used to differentiate healthy patients from patients afflicted with breast cancer.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A method of assessing whether a patient is afflicted with a breast cancer, the method comprising assessing expression of HE4 in a sample, wherein the sample is obtained from the patient or is a fluid that has been brought into contact with a relevant portion of the patient's body, wherein elevated expression of HE4 in the sample, relative to a reference value, is an indication that the patient is afflicted with breast cancer.

2. The method of claim 1, wherein the sample is a solid tissue sample.

3. The method of claim 1, wherein the sample is a body fluid.

4. The method of claim 3, wherein the body fluid is blood or serum.

5. The method of claim 1, wherein the fluid that has been brought into contact with a relevant portion of the patient's body is a lavage fluid, a fluid wash of a probe, scalpel, or biopsy needle that has been brought into contact with the patient's tissue, or a cell or organ culture medium that has been brought into contact with the patient's tissue.

6. The method of claim 1, wherein the reference value corresponds to HE4 expression in patients who are not afflicted with breast cancer.

7. The method of claim 1, wherein the reference value corresponds to HE4 expression in a sample obtained at an earlier time from the patient.

8. The method of claim 1, further comprising assessing expression of a second breast cancer marker in the sample, wherein elevated expression of the second breast cancer marker relative to a reference value for the second breast cancer marker is a further indication that the patient is afflicted with breast cancer.

9. A method of assessing the response of a patient afflicted with a breast cancer to a treatment, the method comprising assessing expression of HE4 in samples obtained at different times during treatment, wherein the samples are obtained from the patient or are fluids that have been brought into contact with a relevant portion of the patient's body, and wherein decreased expression of HE4 in a sample obtained at a later time relative to expression of HE4 in a sample obtained at an earlier time indicates that the patient is responding to the treatment.

10. The method of claim 9, further comprising assessing expression of a second breast cancer marker in the samples, wherein decreased expression of the second breast cancer marker in the sample obtained at the later time relative to expression of the second marker in the sample obtained at the earlier time is a further indication that the patient is responding to the treatment.

11. A method of assessing recurrence of breast cancer in a patient who has been treated for a breast cancer, the method comprising assessing expression of HE4 in a sample obtained prior to treatment and a sample obtained following treatment, wherein the samples are obtained from the patient or are fluids that have been brought into contact with a relevant portion of the patient's body, and wherein elevated expression of HE4 in the sample obtained following treatment relative to HE4 expression in the sample obtained prior to treatment indicates that the breast cancer is recurring in the patient.

12. The method of claim 11, further comprising assessing expression of a second breast cancer marker in the samples, wherein elevated expression of the second breast cancer marker in the sample obtained following treatment relative to expression of the second marker in the sample obtained prior to treatment is a further indication that the breast cancer is recurring in the patient.

13. The method of claim 11, wherein expression of HE4 is assessed multiple times following the treatment, and wherein increasing expression of HE4 in a sample obtained at a later time relative to expression of HE4 in a sample obtained at an earlier time indicates that the breast cancer is recurring in the patient.

* * * * *

SEQUENCE LISTING

```
<160> NUMBER OF SEQ ID NOS: 2

<210> SEQ ID NO 1
<211> LENGTH: 124
<212> TYPE: PRT
<213> ORGANISM: Homo Sapien

<400> SEQUENCE: 1

Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asn Cys Thr Gln Glu
        35                  40                  45

Cys Val Ser Asp Ser Glu Cys Ala Asp Asn Leu Lys Cys Cys Ser Ala
    50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
                85                  90                  95

Cys Gln Val Asp Ser Gln Cys Pro Gly Gln Met Lys Cys Cys Arg Asn
            100                 105                 110

Gly Cys Gly Lys Val Ser Cys Val Thr Pro Asn Phe
        115                 120
```

-continued

```
<210> SEQ ID NO 2
<211> LENGTH: 125
<212> TYPE: PRT
<213> ORGANISM: Homo Sapien

<400> SEQUENCE: 2

Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asn Cys Thr Gln Glu
                35                  40                  45

Cys Val Ser Asp Ser Glu Cys Ala Asp Asn Leu Lys Cys Cys Ser Ala
        50                  55                  60

Gly Cys Ala Thr Phe Cys Leu Leu Cys Pro Asn Asp Lys Glu Gly Ser
65                  70                  75                  80

Cys Pro Gln Val Asn Ile Asn Phe Pro Gln Leu Gly Leu Cys Arg Asp
                85                  90                  95

Gln Cys Gln Val Asp Thr Gln Cys Pro Gly Gln Met Lys Cys Cys Arg
                100                 105                 110

Asn Gly Cys Gly Lys Val Ser Cys Val Thr Pro Asn Phe
            115                 120                 125
```